United States Patent
Torrie et al.

(10) Patent No.: US 7,942,881 B2
(45) Date of Patent: May 17, 2011

(54) MICROFRACTURE PICK

(75) Inventors: Paul Alexander Torrie, Marblehead, MA (US); Marc Philippon, Edwards, CO (US)

(73) Assignee: Smith & Nephew, Inc., Memphis, TN (US)

( * ) Notice: Subject to any disclaimer, the term of this patent is extended or adjusted under 35 U.S.C. 154(b) by 1069 days.

(21) Appl. No.: 11/686,670

(22) Filed: Mar. 15, 2007

(65) Prior Publication Data

US 2007/0270870 A1    Nov. 22, 2007

Related U.S. Application Data

(60) Provisional application No. 60/782,393, filed on Mar. 15, 2006.

(51) Int. Cl.
*A61F 2/46* (2006.01)
(52) U.S. Cl. .................. 606/86 R; 606/83; 606/167
(58) Field of Classification Search ............... 606/86 R, 606/83, 84, 184; 30/168, 167
See application file for complete search history.

(56) References Cited

U.S. PATENT DOCUMENTS

| | | | | |
|---|---|---|---|---|
| 5,135,528 | A | * | 8/1992 | Winston .................. 606/79 |
| 5,375,332 | A | * | 12/1994 | Judge .................. 30/366 |
| 5,921,987 | A | | 7/1999 | Stone |
| 6,352,558 | B1 | | 3/2002 | Spector |
| 6,960,214 | B2 | | 11/2005 | Burkinshaw |
| 7,387,637 | B2 | * | 6/2008 | Morawski et al. ........... 606/167 |
| 2004/0073223 | A1 | | 4/2004 | Burkinshaw |
| 2004/0147932 | A1 | | 7/2004 | Burkinshaw et al. |

OTHER PUBLICATIONS

PCT International Search Report and the Written Opinion; PCT/US2007/064086.

* cited by examiner

*Primary Examiner* — Thomas C Barrett
*Assistant Examiner* — Andrew Yang
(74) *Attorney, Agent, or Firm* — Norman F. Hainer, Jr.

(57) ABSTRACT

The present disclosure relates to a microfracture pick having a shaft and a handle. The shift has a proximal end and a distal end, wherein the distal end includes an angled tip. The handle has a body with a first end portion, a second end portion, and an impact surface located therebetween. The handle is operatively coupled to the proximal end of the shaft at the first end portion. Methods of microfracture stimulation are also disclosed.

5 Claims, 9 Drawing Sheets

MICROFRACTURE PICK

CROSS-REFERENCE TO RELATED APPLICATIONS

This application claims the benefit of U.S. Provisional Application No. 60/782,393, filed Mar. 15, 2006, the disclosure of which is incorporated by reference in its entirety.

BACKGROUND OF THE INVENTION

1. Field of the Invention

The present disclosure relates to microfracture stimulation and, more particularly, to a device for use in microfracture stimulation.

2. Related Art

Articulating body joints are surfaced with hyaline cartilage, which is a very durable low coefficient of friction natural material. These surfaces are often damaged when subjected to high repeated loading, such as when one runs. This is particularly true for lower body compressive joints such as the ankle, knee, hip and spine.

Resurfacing of the cartilage surfaces is a large area of study in the orthopaedic industry. One method is called microfracture. Rather than replacing the damaged articular cartilage with an artificial implant, microfracture stimulates the body to replace the surface with a fibrous cartilage. Fibrocartilage is not as robust and does not have the low coefficient of friction that hyaline cartilage does, but it does provide patients with reduced pain and enables then to participate in an active lifestyle.

Microfracture is created by first removing the damaged layer of cartilage. The damaged layer can vary from about 1 to about 6 mm in thickness. A sharp microfracture pick is then driven down about 2 to about 5 mm through the underlying subchondral bone to a blood supply. When the pick is removed, a small channel remains. Blood travels along the channels and clots in the area of the removed cartilage. The technique requires a series of such channels in the area of removed cartilage.

Microfracture pick have been created for use in this technique. The picks come with a sharp tip bent at various angles relative to the long axis of the pick's shaft. Typically, microfracture picks are available with tips having angles 20, 40, 60 or 90 degrees.

Figure 1:
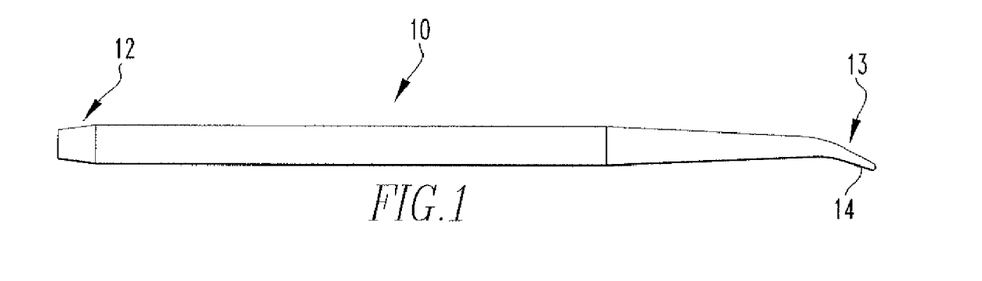
FIG. 1 is a first embodiment of a prior art device.
Figure 2:
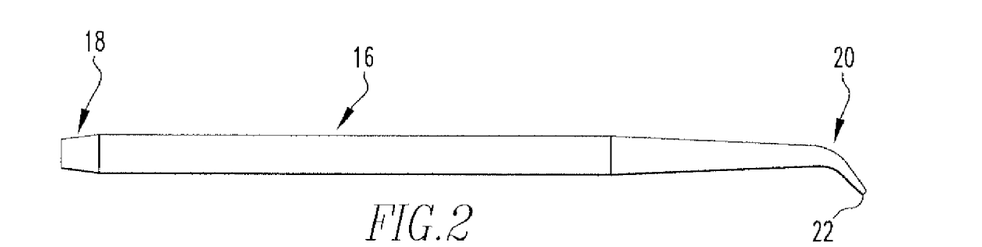
FIG. 2 is a second embodiment of a prior art device.

FIGS. 1 and 2 illustrate two prior art microfracture picks 10, 16. Each pick 10, 16 has a proximal end 12, 18 and a distal end 13, 20. Further, each pick 10, 16 has a sharp bent tip 14, 22 on its distal end 13, 20. The second pick 16 is identical to the first pick 10 except the second pick 16 has a tip 22 bent at a sharper angle.

Figure 3:
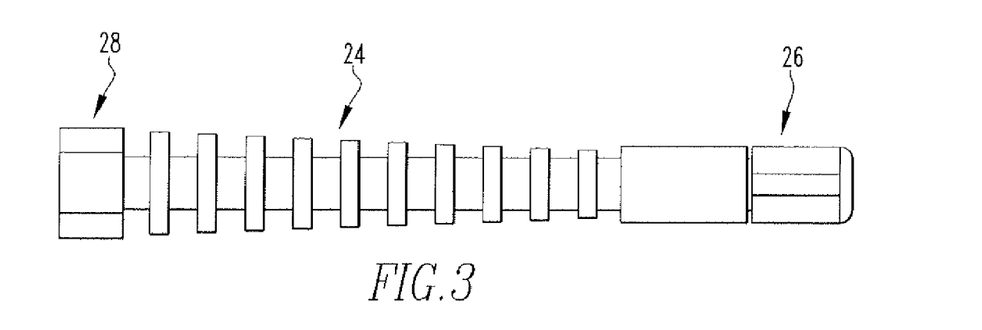
FIG. 3 is a handle for use with the devices shown in FIGS. 1 and 2.

FIG. 3 illustrates a handle 24 that is adapted for use with either the first pick 10 or the second pick 16. The handle 24 has an impact end 28 and a receiver end 26. The receiver end 26 includes a hole (not shown) to receive the proximal end 12, 18 of the picks 10, 16. In use, a surgeon assembles the pick 10, 16 to the handle 24, places the tip 14, 22 at the desired location for a channel, and hits the impact end 28 with a striking mass (not shown) until the tip 14, 22 is inserted approximately 2 to 5 mm through the underlying subchondral bone.

Since the handle 24 is designed to be struck on the impact end 28, the force is transmitted axially from the impact end 28 through a shaft of the pick 10, 16 and finally to the tip 14, 22. As the tip angle approaches 90 degrees, the axial impact does not transmit a force that acts in the direction of the tip. The result is that an elongated hole is made in the subchondral bone, which is not ideal, and it takes longer to get down to the blood supply. Additionally, when the tip is engaged in the subchondral bone and the proximal handle is struck with a striking mass, the tip is under large stress.

Therefore, there remains a need in the art for a microfracture pick that allows force to be transmitted in the direction of the tip even when the tip angle approaches 90 degrees.

SUMMARY OF THE INVENTION

In one aspect, the present disclosure relates to a microfracture pick including a shaft having a proximal end and a distal end, the shaft having an angled tip at the distal end, and a handle having a body, the body having a first end portion, a second end portion, and an impact surface located therebetween. The handle is operatively coupled to the proximal end of the shaft at the first end portion. In an embodiment, the pick further includes a weight operatively coupled to the second end portion, such that the second end portion has more mass than the first end portion. In another embodiment, the pick further includes a wear plate mounted to the impact surface. In yet another embodiment, the handle, wherein at least a portion of which includes plastic or metal, is mounted on an angle $\theta$ relative to the shaft and includes grooves. The angle $\theta$ is between about 0 degrees to about 45 degrees. In a further embodiment, the impact surface is located adjacent to the first end portion. In one embodiment, the body is cylindrical or non-cylindrical and the shaft includes stainless steel.

In a second aspect, the present invention disclosure relates to a method of microfracture stimulation. The method includes the steps of providing a microfracture pick having a shaft with a proximal end and a distal end, the shaft having angled tip at the distal end, and a handle having a body, the body having a first end portion, a second end portion, and an impact surface located therebetween, wherein the handle is operatively coupled to the proximal end of the shaft at the first end portion; locating the tip at a desired point of stimulation; striking the impact surface; and removing the tip. In an embodiment, the step of locating the tip at a desired point of stimulation includes the step of inserting at least a portion of the shaft into an arthroscopic cannula. In an embodiment, the step of striking the impact surface includes striking the impact surface in a direction generally parallel to a direction of the tip.

In a third aspect, the present disclosure relates to a surgical device having a proximal portion including a handle, a distal portion including a shaft, the distal portion having an end, wherein the end includes an angled tip, and an impact surface located between the proximal portion and the distal portion. The surgical device includes a one piece construction.

In a fourth aspect, the present disclosure relates to a surgical device having a proximal portion including a first end, a second end, and an impact surface located therebetween, and a distal portion including a first end and a second end, the second end operatively coupled to the first end of the proximal portion, the first end including an angled tip. In one embodiment, the impact surface is located adjacent to the first end of the proximal portion. In another embodiment, the proximal portion is mounted on an angle $\theta$, which is between about 0 degrees to about 45 degrees, relative to the distal portion. In yet another embodiment, the tip is angled relative to the distal portion at an angle $\alpha$, which is between about 20 degrees to about 90 degrees. In a further embodiment, the surgical device includes a microfracture pick. In yet a further embodiment, surgical device includes a sheath, having at least one channel, wherein the angled tip of the first end of the distal portion is located within the channel. The sheath may include a groove.

In a fifth aspect, the present disclosure relates to a method of performing a microfracture procedure. The method includes the steps of providing a surgical device having a proximal portion including a first end, a second end, and an impact surface located therebetween, and a distal portion including a first end and a second end, the second end operatively coupled to the first end of the proximal portion and the first end including an angled tip; locating the tip at a desired point of stimulation; striking the impact surface; and removing the tip. In an embodiment, the step of striking the impact surface includes striking the impact surface in a direction generally parallel to the direction of the tip.

In a sixth aspect, the present disclosure relates to a surgical device having a proximal portion including a first end, a second end, and an impact surface located therebetween, and a distal portion comprising a first end and a second end, the second end operatively coupled to the first end of the proximal portion, the first end angled relative to the distal portion at an angle β. In an embodiment, the angle β is about 90 degrees. In another embodiment, the first end of the distal portion forms a pointed tip.

Further areas of applicability of the present disclosure will become apparent from the detailed description provided hereinafter. It should be understood that the detailed description and specific examples, while indicating the preferred embodiment of the present disclosure, are intended for purposes of illustration only and are not intended to limit the scope of the present disclosure.

BRIEF DESCRIPTION OF THE DRAWINGS

The present disclosure will become fully understood from the detailed description and the accompanying drawings, wherein:

FIG. 11b shows a cross-section of the sheath/microfracture pick combination shown in FIG. 11a.

DETAILED DESCRIPTION OF THE PREFERRED EMBODIMENTS

The following description of the preferred embodiment(s) is merely exemplary in nature and is in no way intended to limit the present disclosure, its application, or uses.

Figure 4:
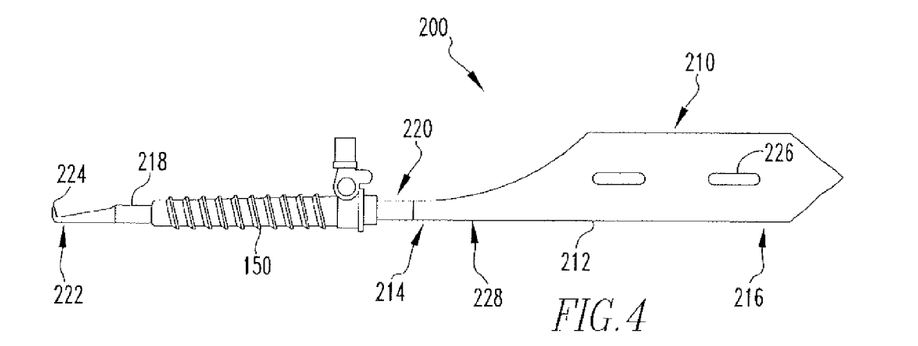
FIG. 4 is a side view illustrating a first embodiment of the present disclosure.

FIG. 4 illustrates a first embodiment of the surgical device 200, such as a microfracture pick, of the present disclosure. The microfracture pick 200 includes a proximal portion 210, such as a handle, and a distal portion 218, such as a shaft. In the embodiment depicted in FIG. 4, the handle 210 is substantially thin and substantially flat. As examples, the handle 210 may have a variety of shapes, including, but not limited to, a rectangle, a square, an oval, or a polygon. The handle 210 has a body 212, a first end portion 214, and a second end portion 216. An impact surface 228 is located between the handle 210 and the shaft 218. In some embodiments, the handle 210 may also include cutouts 226, such as holes, slots, or other apertures to aid in cooling after autoclaving. The shaft 218 includes a first end 222 and a second end 220. The shaft 218 also has a tip 224 on the first end portion 222. The second end 220 of the shaft 218 may be operatively coupled to the first end 214 of the handle 210 or the surgical device 200 may have a one-piece construction wherein the handle 210, shaft 218, and impact surface 228 are integral with one another rather than being separate components.

Figure 5:
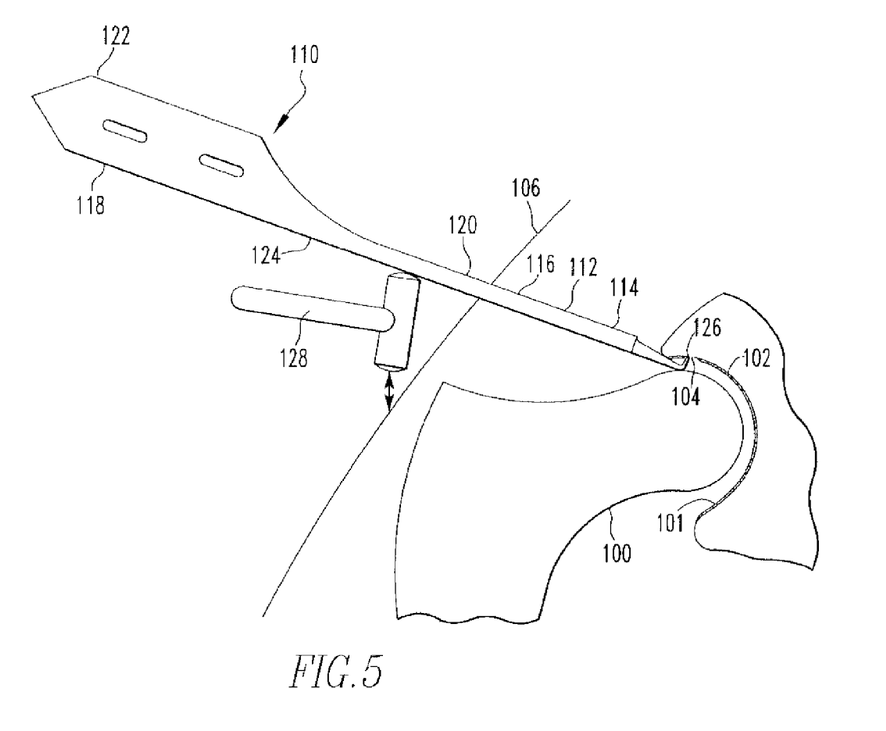
FIG. 5 is a side view illustrating use of the first embodiment of the present disclosure.

FIG. 5 is a side view illustrating use of the first embodiment 110 of the present disclosure. As an example, the microfracture pick 110 may be used to create a channel (not shown) for the production of fibrocartilage in between an acetabular cup 102 and a femur 100. The tip 126 is located in an area 104 where there is a break in the cartilage layer 101 and where cartilage no longer exists. In operation, the microfracture pick 110 is first placed in its proper position. In the example of hip arthroscopy, the microfracture pick 110 may be inserted through an arthroscopic cannula (FIG. 4, 150) through skin 106 until the tip 126 is properly located. After the microfracture pick is located, a striking mass 128, such as a hammer, mallet, or other mass, is used to strike the impact surface 124 in order to drive the tip 126 between about 2 mm to about 5 mm through the underlying subchondral bone. Because the microfracture pick 110 is impacted in a direction generally parallel to the tip 126 rather than axially through the shaft 112, penetration of the tip 126 is more effective. In other words, energy from the striking mass 128 is transferred in the direction in which it is needed by impacting the microfracture pick 110 on its impact surface 124.

Figure 6:
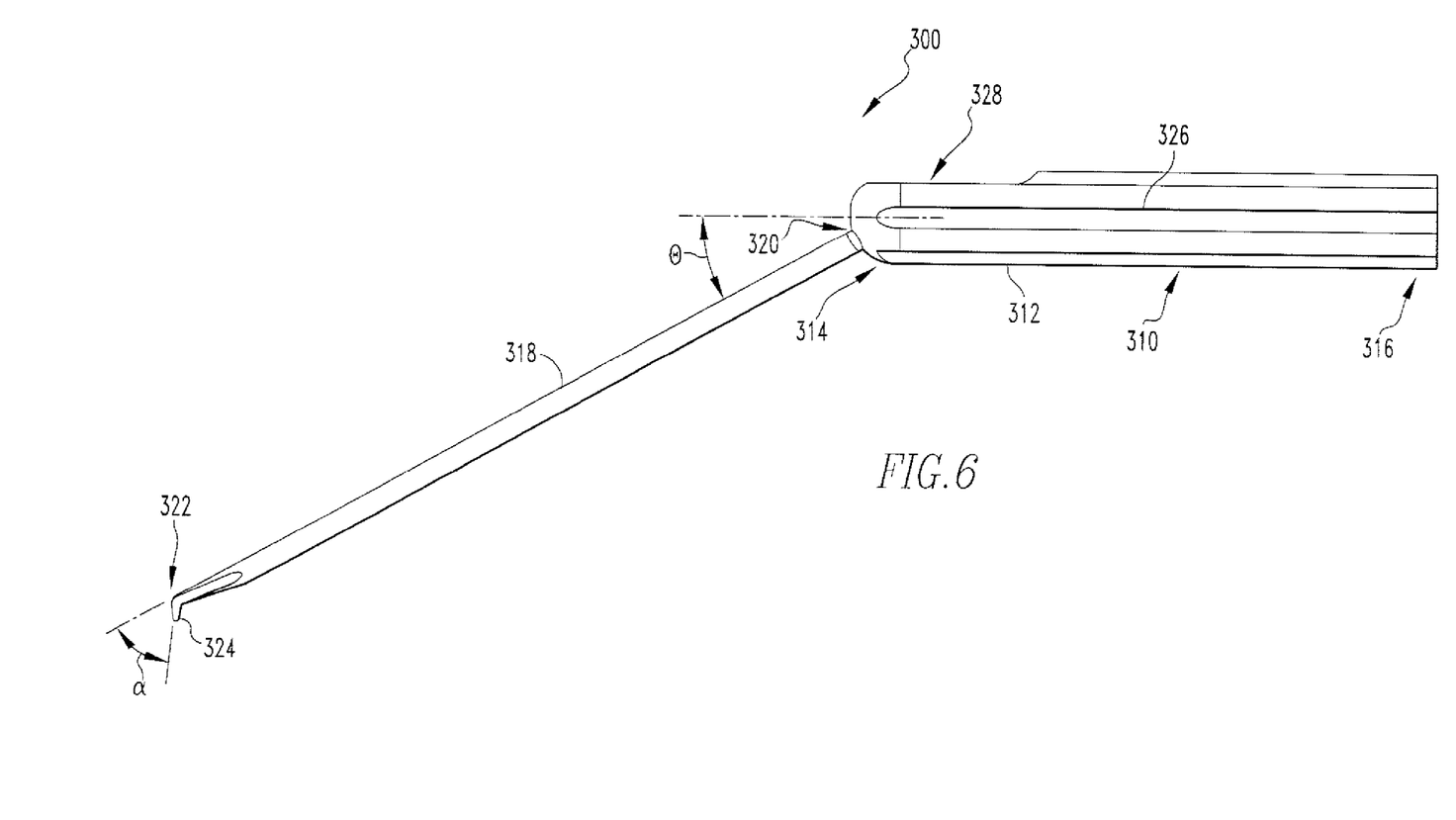
FIG. 6 is side view illustrating a second embodiment of the present disclosure.
Figure 8:
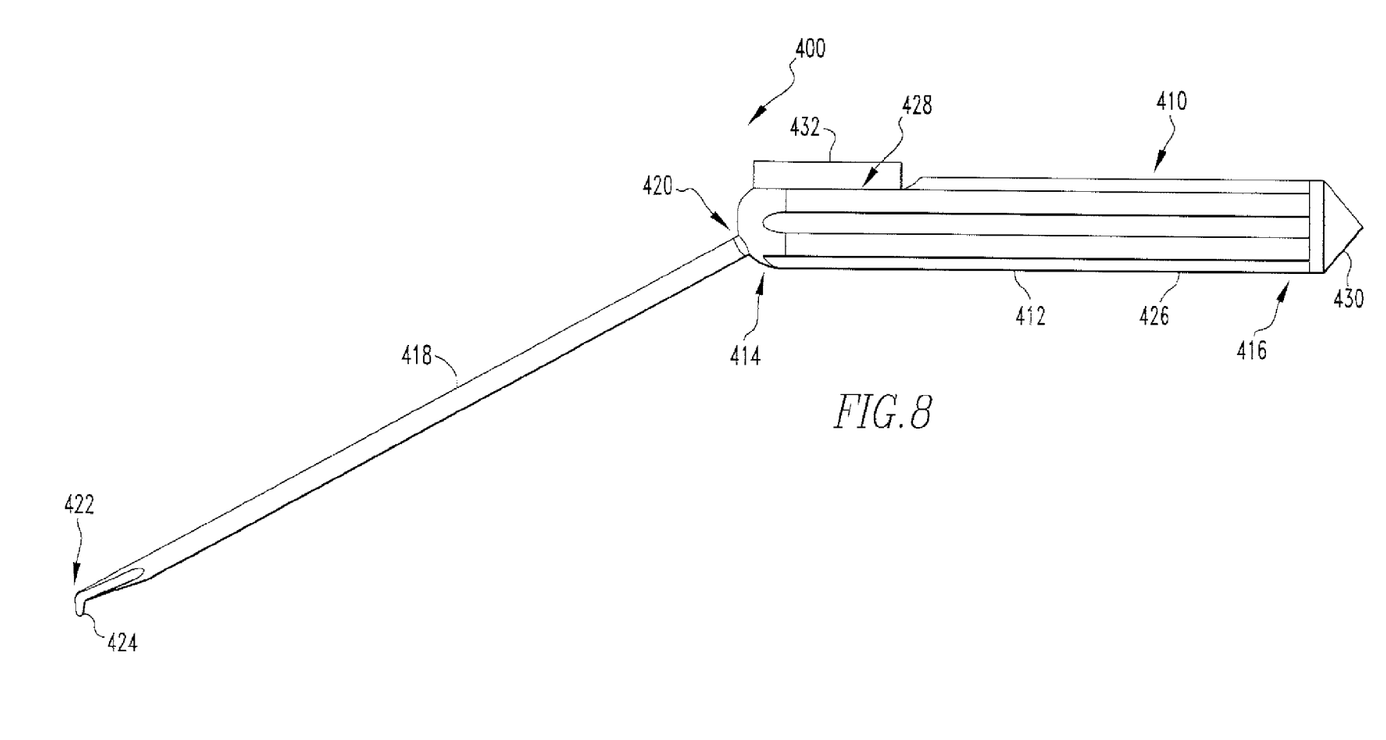
FIG. 8 is a side view illustrating a third embodiment of the present disclosure.

As can be seen in FIG. 5, there is a limited amount of space between the patient's skin 106 and the impact surface 124. Thus, there is little room to swing the striking mass 128. FIGS. 6 and 8 illustrate a second and a third embodiment of the microfracture pick 300, which addresses this issue. The microfracture pick 300 includes a proximal portion 310, such as a handle, and a distal portion 318, such as a shaft. In the embodiment depicted in FIG. 6, the handle 310 is substantially cylindrical. The handle 310 includes a first end portion 314, a second end portion 316, and an impact surface 328 located between the first end portion 314 and the second end portion 316. Optionally, the handle 310 may also include longitudinal grooves 326. The shaft 318 includes a first end portion 322 and a second end portion 320. The shaft 318 also has an angled tip 324 on the first end portion 322. The tip 324 is angled relative to the shaft 318 at an angle α, or between about 20 degrees to about 90 degrees. In the embodiment depicted in FIG. 6, the shaft 318 tapers at the first end portion 322. Also, the handle 310 is mounted on an angle θ, which is between about 0 degrees to about 45 degrees, relative to the shaft 318.

Figure 7:
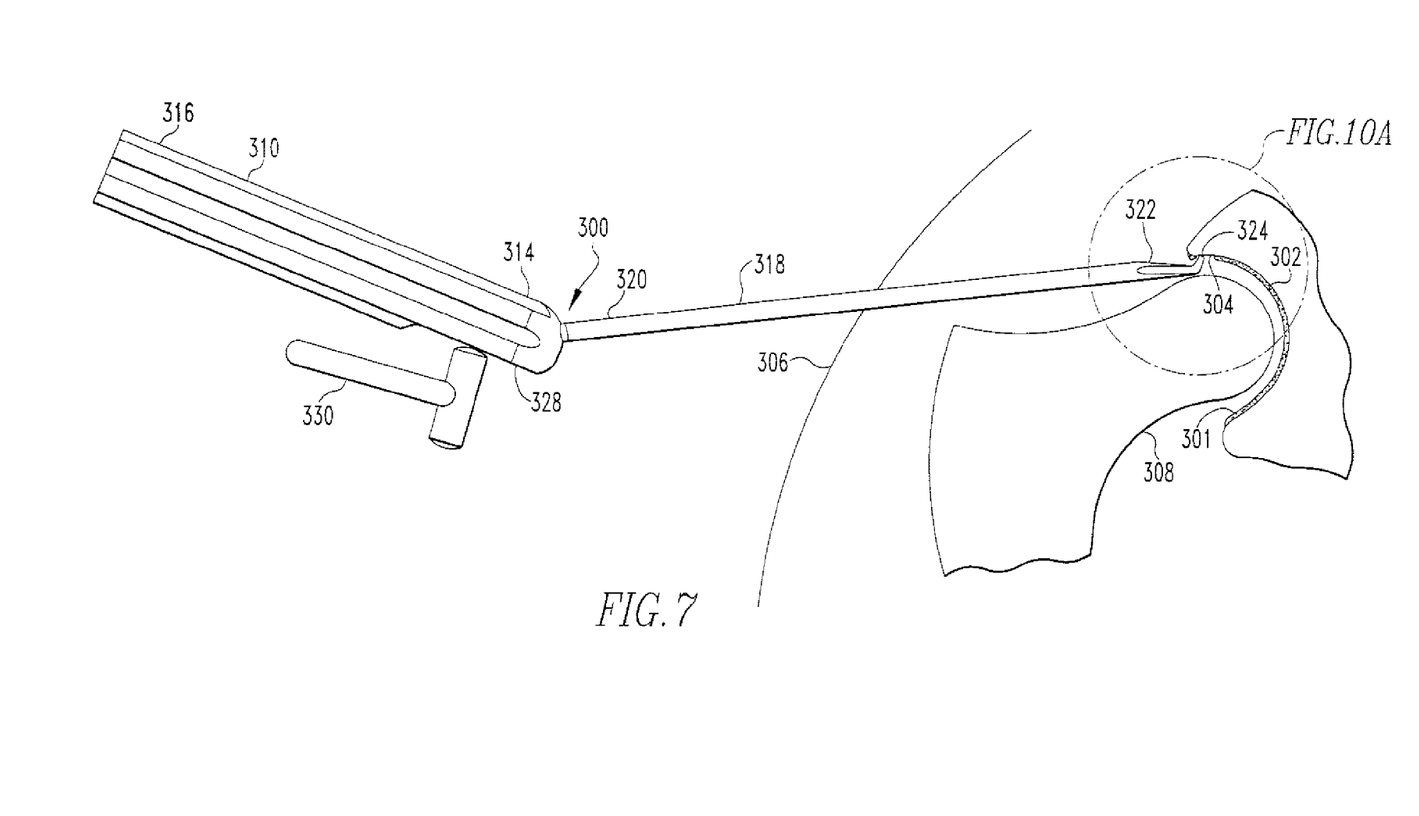
FIG. 7 is a side view illustrating use of the second embodiment of the present disclosure

As shown in FIG. 7, in operation, the microfracture pick 300 is first placed in its proper position. The tip 324 is located in an area 304 where there is a break in the cartilage layer 301 and where cartilage no longer exists. After the microfracture pick is located, a striking mass 330 is used to strike the impact surface 328 in order to drive the tip 324 between about 2 mm to about 5 mm through the underlying subchondral bone. With the handle 310 being mounted at an angle relative to the shaft 318, there is more room available, between the skin and the impact surface, to swing the striking mass.

FIG. 8 illustrates a third embodiment of the microfracture pick 400. The microfracture pick 400 includes a handle 410 and a shaft 418. The handle 410 has a body 412, a first end portion 414, and a second end portion 416. The handle 410 includes an impact surface 428 located between the first end portion 414 and the second end portion 416. Optionally, the handle 410 may also include longitudinal grooves 426. The shaft 418 includes a proximal end portion 420 and a distal end portion 422. The shaft 418 also has an angled tip 424 on the distal end portion 422. Optionally, the microfracture pick 400 may include a wear plate 432 that is removably coupled to the impact surface 428. As the wear plate 432 wears out, the wear plate 432 can be removed and replaced without replacing the entire body 412 of the microfracture pick 400. The handle 410 may be made from metal or plastic. In the embodiment depicted in FIG. 8, the handle 410 is made of hardened stainless steel. To further increase the mass of the handle 410, a weight 430 may be coupled to the second end portion 416. The weight 430 may be integral or it may be a separate component removably attached to the body 412. The microfracture pick 400 is very similar in operation to the pick 300 in FIG. 6.

Figure 9:
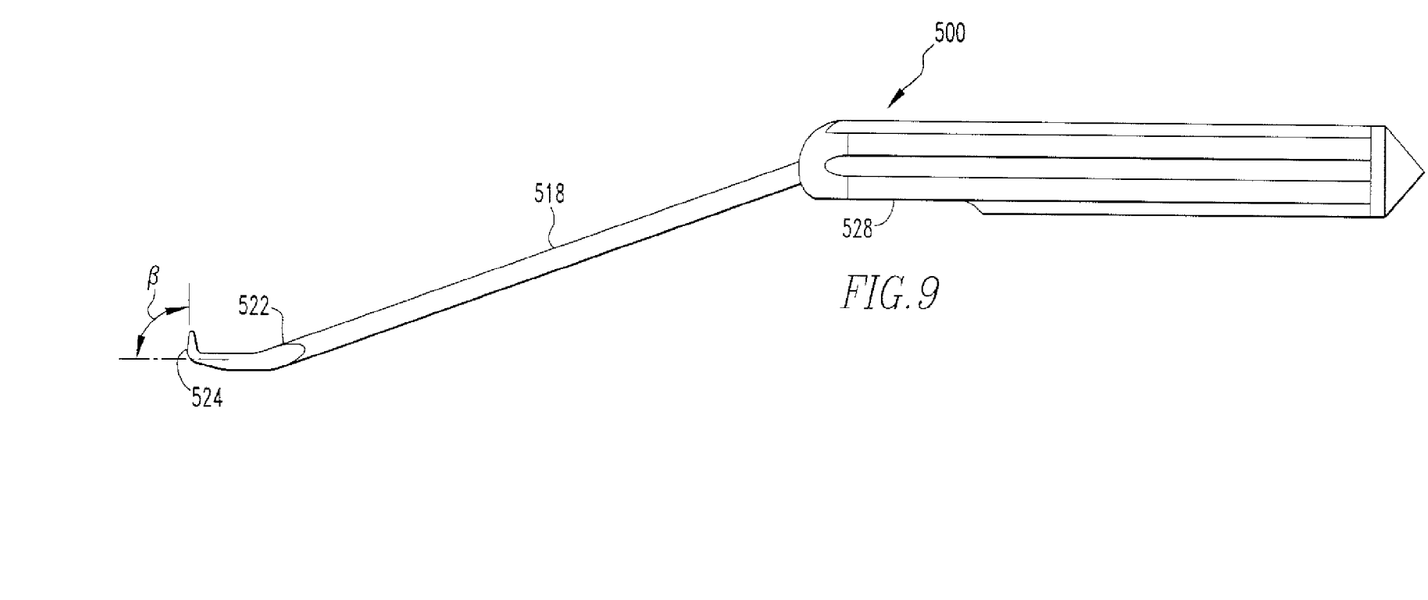
FIG. 9 is a side view illustrating a fourth embodiment of the present disclosure.
Figure 10A:
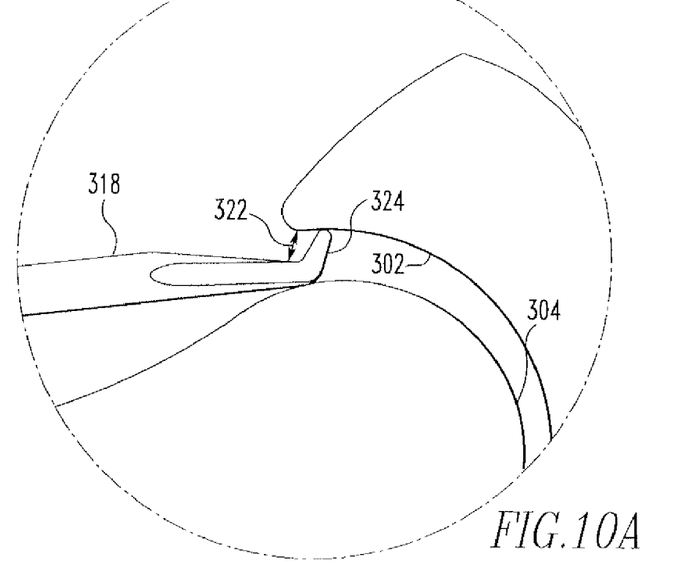
FIG. 10a is an enlarged detailed view of the angled tip of the second embodiment during use in microfracture stimulation.
Figure 10B:
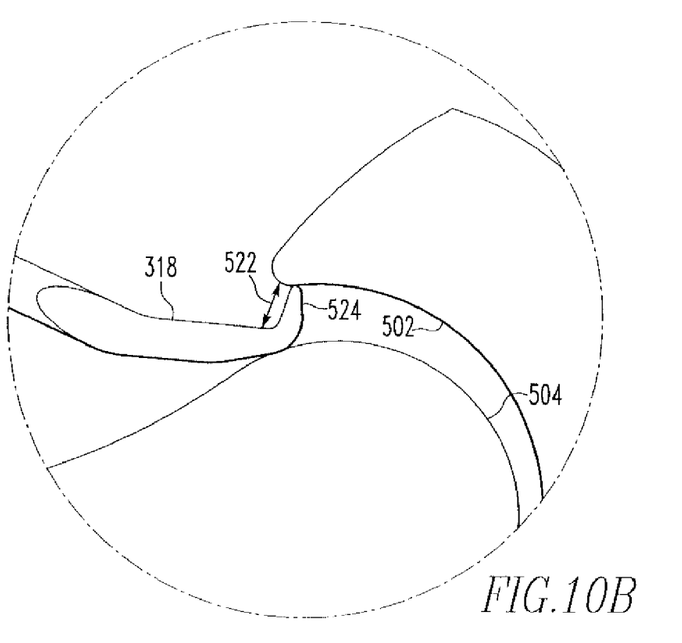
FIG. 10b is an enlarged detailed view of the angled tip of the fourth embodiment during use in microfracture procedure.

FIG. 9 illustrates a fourth embodiment of a surgical device 500, such as a microfracture pick, of the present disclosure. The pick 500 is similar to the pick 300 shown in FIG. 6, but instead of having a distal portion 518, or a shaft, with a first end 522 that is straight, the first end 522 is curved or angled relative to the distal portion at an angle β, which is about 90 degrees, and includes a pointed tip 524. As shown in FIGS. 10a and 10b, this makes for less contact between the inner portion of the first end 522 and the acetabular cup when the impact surface 528 is struck with a striking mass (best shown in FIGS. 5 and 7).

Figure 11A:
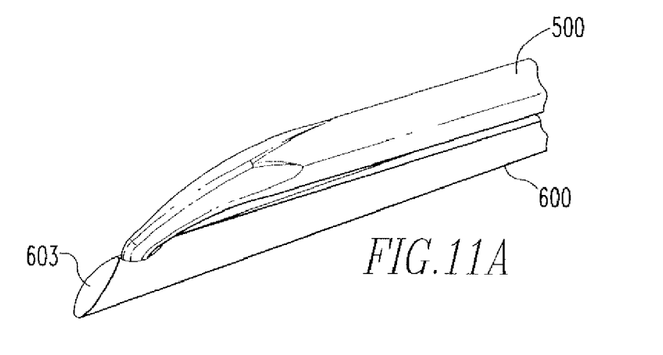
FIG. 11a shows a first embodiment of a sheath that is used with the microfracture pick of the present disclosure.
Figure 11B:
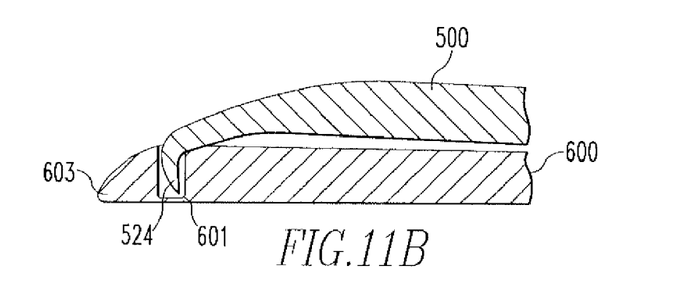
Figure 12A:
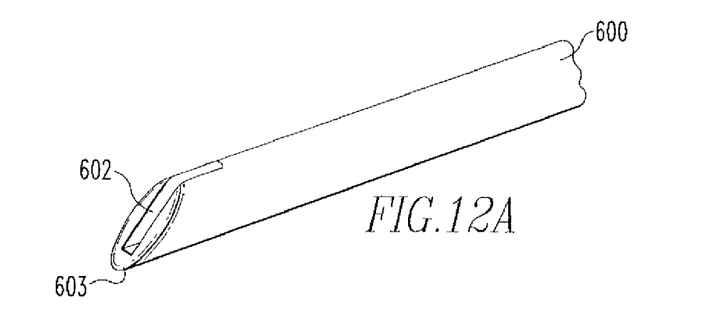
FIG. 12a shows a second embodiment of a sheath that is used with the microfracture pick of the present disclosure.
Figure 12B:
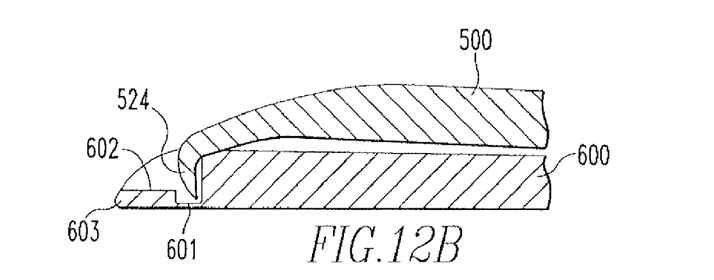
FIG. 12b shows a cross section of the sheath of FIG. 12a as used with the microfracture pick of the present disclosure.
Figure 13:
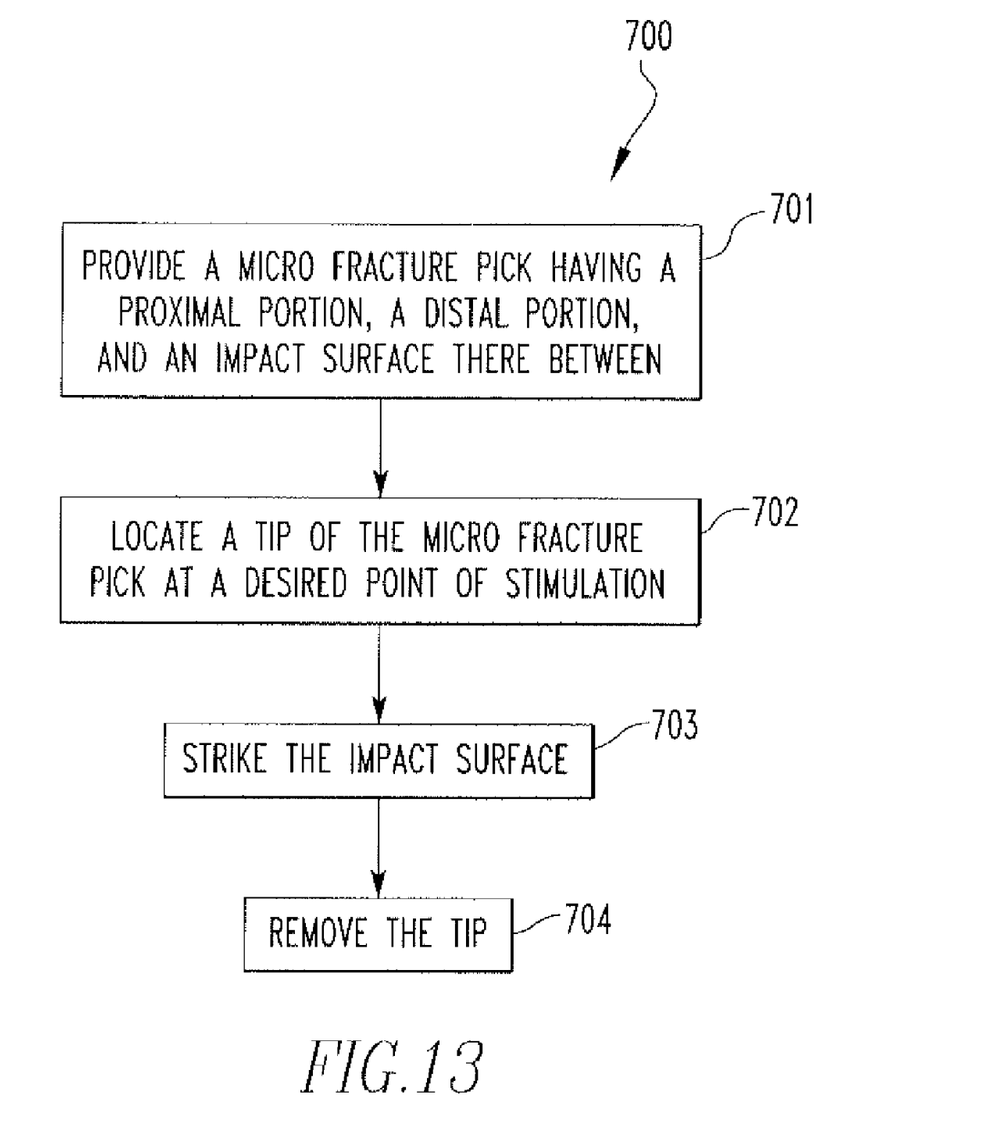
FIG. 13 shows a method of microfracture stimulation of the present disclosure.

As shown in FIGS. 11a-11b and 12a-12b, the surgical device 500 of the present disclosure may include a sheath 600. For simplicity purposes, only the distal end 603 of the sheath 600 is shown. However, the sheath 600 may extend the entire length of the surgical device 500 and include a proximal portion having a handle. As shown in FIGS. 11a-11b, the sheath 600 includes a channel 601 that houses the pointed tip 524 of the surgical device 500. As shown in FIGS. 12a-12b, the sheath may also include a groove 602. The groove 602 may be located distal of the channel 601, as shown in FIG. 12b, but may also be located proximal or peripheral of the channel 601. In use, the tip 524 is dislodged from the channel 601, after the device 500 is placed in the patient's body, and the sheath 600 is removed. The tip 524 may be dislodged from the channel 601 by moving or bending the handle (not shown) of the sheath 600 and/or the device 500 or by pushing the device 500 toward the distal end 603 of the sheath 600 to locate the pointed tip 524 in the groove 602 for subsequent removal of the device 500. The sheath 501 includes a plastic material and is manufactured via a fabrication process, but may include another material or be manufactured via another process known to one of ordinary skill in the art. By including the sheath 600, the pointed tip 524 of the device 500 is protected from scraping against a cannula during insertion of the device 500 into a portal, thereby substantially reducing the possibility of dulling the tip 524. In addition, the sheath 600 also reduces the possibility of the tip 524 catching on soft tissue as the device 500 is rotated out of a slotted cannula. The channel 601 has a width of about 0.090 inches.

As shown in FIG. 12, the present disclosure further includes a method of microfracture stimulation on a patient 700. A first step of the method is to provide a microfracture pick with an impact surface located between the proximal end portion and the distal end portion of the microfracture pick 701. The second step is to locate a tip of the microfracture pick at a desired point of stimulation 702. This step may include insertion of at least a portion of the microfracture pick into a standard arthroscopic cannula. The third step is to strike the impact surface with a striking mass until the tip is driven between about 2 mm to about 5 mm through the underlying subchondral bone to a blood supply 703. This step may include striking the impact surface in a direction generally parallel to a direction of the tip. A fourth step is to remove the tip 704, thereby leaving a small channel in the underlying subchondral bone. Eventually, blood will travel in the channel to form fibrous cartilage.

As various modifications could be made to the exemplary embodiments, as described above with reference to the corresponding illustrations, without departing from the scope of the present disclosure, it is intended that all matter contained in the forgoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A method of performing a microfracture procedure, the method comprising the steps of:
   providing a surgical device having a proximal portion comprising a first end, a second end, and an impact surface located therebetween, and a distal portion comprising a first end and a second end, the second end operatively coupled to the first end of the proximal portion, the first end including an angled tip;
   locating the tip at a desired point of stimulation;
   striking the impact surface; and
   removing the tip.

2. The method of claim 1 wherein the step of striking the impact surface includes striking the impact surface in a direction generally parallel to a direction of the tip.

3. A method of microfracture stimulation, the method comprising the steps of:
   providing a microfracture pick having a shaft with a proximal end and a distal end, the shaft having an angled tip at the distal end, and a handle having a body, the body having a first end portion, a second end portion, and an impact surface located therebetween, and the handle is operatively coupled to the proximal end of the shaft at the first end portion;
   locating the tip at a desired point of stimulation;
   striking the impact surface; and
   removing the tip.

4. The method of claim 3, wherein the step of locating the tip at a desired point of stimulation includes the step of inserting at least a portion of the shaft into an arthroscopic cannula.

5. The method of claim 3, wherein the step of striking the impact surface includes the step of striking the impact surface in a direction generally parallel to a direction of the tip.

* * * * *